United States Patent
Yanuma

(10) Patent No.: US 11,426,232 B2
(45) Date of Patent: Aug. 30, 2022

(54) TREATMENT INSTRUMENT AND ENDOSCOPIC SYSTEM

(71) Applicant: Olympus Corporation, Hachioji (JP)

(72) Inventor: Yutaka Yanuma, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 191 days.

(21) Appl. No.: 16/789,721

(22) Filed: Feb. 13, 2020

(65) Prior Publication Data

US 2020/0179039 A1 Jun. 11, 2020

Related U.S. Application Data

(63) Continuation of application No. PCT/JP2017/032055, filed on Sep. 6, 2017.

(51) Int. Cl.
*A61B 1/00* (2006.01)
*A61B 18/14* (2006.01)
(Continued)

(52) U.S. Cl.
CPC ...... *A61B 18/1482* (2013.01); *A61B 1/00133* (2013.01); *A61B 1/00135* (2013.01);
(Continued)

(58) Field of Classification Search
None
See application file for complete search history.

(56) References Cited

U.S. PATENT DOCUMENTS

| 4,846,175 A | 7/1989 | Frimberger |
| 4,934,340 A * | 6/1990 | Ebling ................. A61B 1/0058 600/117 |

(Continued)

FOREIGN PATENT DOCUMENTS

| EP | 0 019 930 A1 | 12/1980 |
| JP | S61-004325 Y2 | 2/1986 |

(Continued)

OTHER PUBLICATIONS

Nov. 28, 2017 International Search Report issued in International Patent Application No. PCT/JP2017/032055.
(Continued)

*Primary Examiner* — Timothy J Neal
(74) *Attorney, Agent, or Firm* — Oliff PLC

(57) ABSTRACT

The disclosed technology is directed to a treatment instrument that comprises a sheath main body having opposed respective distal and proximal end regions. The sheath main body includes an outer diameter such that the sheath main body capable of being fit into the channel for insertion of the treatment instrument of the endoscope. The sheath main body includes a lumen extending along a longitudinal axis in the distal end region. A wire-shaped incising portion is configured to engage with the sheath main body so as to protrude from an outer circumferential surface of the sheath main body in the distal end region and extending along the longitudinal axis of the sheath main body. The wire-shaped incising portion is used to incise a tissue. A wire is attached to at least a portion of the sheath main body and having a region in which the wire has different bending resistances.

8 Claims, 12 Drawing Sheets

(51) Int. Cl.
    *A61B 1/01* (2006.01)
    *A61B 17/221* (2006.01)
    *A61B 17/00* (2006.01)
    *A61B 18/00* (2006.01)

(52) U.S. Cl.
    CPC .............. *A61B 1/01* (2013.01); *A61B 17/221* (2013.01); *A61B 2017/00818* (2013.01); *A61B 2017/2215* (2013.01); *A61B 2018/00083* (2013.01); *A61B 2018/00494* (2013.01); *A61B 2018/00601* (2013.01); *A61B 2018/00982* (2013.01)

(56) References Cited

U.S. PATENT DOCUMENTS

| | | | |
|---|---|---|---|
| 5,024,617 | A | 6/1991 | Karpiel |
| 5,163,938 | A | 11/1992 | Kambara et al. |
| 6,017,339 | A | 1/2000 | Sadamasa |
| 6,471,702 | B1 | 10/2002 | Goto |
| 6,712,817 | B1 | 3/2004 | Goto et al. |
| 7,371,237 | B2 | 5/2008 | Hutchins et al. |
| 8,998,825 | B2 | 4/2015 | Matsuno et al. |
| 9,345,539 | B2 | 5/2016 | Yanuma |
| 9,352,124 | B2 | 5/2016 | Hutchins et al. |
| 9,480,818 | B2 | 11/2016 | Hollett |
| 9,706,904 | B2 | 7/2017 | Matsuno et al. |
| 9,974,610 | B2 | 5/2018 | Oguni et al. |
| 10,045,818 | B2 | 8/2018 | Kobayashi et al. |
| 2005/0261675 | A1 | 11/2005 | Shibata |
| 2007/0162101 | A1* | 7/2007 | Burgermeister .. A61M 25/0105 623/1.11 |
| 2009/0048487 | A1* | 2/2009 | Yanuma ............. A61B 18/1492 600/139 |
| 2009/0254084 | A1 | 10/2009 | Naito |
| 2015/0342633 | A1 | 12/2015 | Yanuma et al. |
| 2016/0331454 | A1 | 11/2016 | Kobayashi et al. |
| 2019/0038376 | A1 | 2/2019 | Yanuma |

FOREIGN PATENT DOCUMENTS

| | | |
|---|---|---|
| JP | S63-288150 A | 11/1988 |
| JP | H02-279151 A | 11/1990 |
| JP | H04-364836 A | 12/1992 |
| JP | H09-206309 A | 8/1997 |
| JP | 3482379 B2 | 12/2003 |
| JP | 2005-334000 A | 12/2005 |
| JP | 2009-247696 A | 10/2009 |
| JP | 2015-008827 A | 1/2015 |
| JP | 5911652 B2 | 4/2016 |
| JP | 2016-093226 A | 5/2016 |

OTHER PUBLICATIONS

Nov. 28, 2017 Written Opinion of the International Searching Authority issued in International Patent Application No. PCT/JP2017/032055.

Dec. 8, 2020 Office Action issued in Japanese Patent Application No. 2019-540174.

* cited by examiner

TREATMENT INSTRUMENT AND ENDOSCOPIC SYSTEM

CROSS-REFERENCE TO RELATED APPLICATION

This application is a continuation application of PCT Application No. PCT/JP2017/032055 filed on Sep. 6, 2017, which is hereby incorporated by reference in its entirety.

TECHNICAL FIELD

The disclosed technology relates to a treatment instrument for use in combination with an endoscope having an elevator at a distal end portion of a channel, and also to an endoscope system including the treatment instrument.

DESCRIPTION OF THE RELATED ART

When an endoscope is used for removal of bile duct stones, some of the stones may not be removed due to large sizes which is larger than a narrow opening of a duodenal papilla. In such a situation, sphincter muscles are incised by a treatment instrument incorporated with an endoscope, such as a papillotome disclosed, for example, in JP 2005-334000 A (aka, PTL 1) and U.S. Pat. No. 7,371,237 (aka, PTL 2), as inserted in the endoscope, and after widening the exit of the bile duct, the stones are retrieved.

A position of an encircling fold is substantially coincident with the direction in which the bile duct extends around the duodenal papilla. Since blood vessels are sparse and bleeding hardly occurs in this direction, sphincter muscles are generally incised in the direction of the encircling fold.

Now, with an endoscope suited for treatment of a gallbladder and a pancreas, an image is available with a bile duct oriented at approximately the 12 o'clock marker when an endoscopic image is acquired by inserting the endoscope into a duodenum. An endoscope of this kind includes an elevator that can move a papillotome up and down in a direction of the 12 o'clock marker.

Upon incision, an incising portion of a papillotome is pulled taut by a manipulation on a side proximal to a surgeon. The incising portion separates from a sheath, and only the incising portion is then pressed against the duodenal papilla. As a consequence, a large pressure arises between the incising portion and mucosa of a part to be incised. When an elevator is driven while the incising portion is energized, the papillotome moves at a distal end thereof in the direction of the 12 o'clock marker and the duodenal papilla is then incised.

If a bile duct has a morphologic characteristic or the like, if there is a constriction in an adjacent organ such as a duodenum, if a patient has received a surgical operation on an adjacent organ such as a duodenum in the past, or in a similar case, on the other hand, a direction of a bile duct in the vicinity of a duodenal papilla may differ from the 12 o'clock direction of an endoscope screen.

For purpose of also facilitating incision in a direction other than the 12 o'clock direction on an endoscope screen, a conventional papillotome therefore includes a torque transmission member to transmit a rotational torque from a side proximal to a surgeon. The papillotome is hence configured to enable transmission of a rotational torque, which rotates a sheath at a proximal end side thereof about its axis, to a distal end of a knife portion.

In a papillotome for use in such incision of sphincter muscles, it is desired that a direction of a knife portion, i.e., a distal end portion of a sheath main body is automatically oriented at approximately the 12 o'clock marker of an endoscope screen when caused to protrude from a distal end of a cholangiopancreatic endoscope.

An insertion portion of an endoscope is inserted from a mouth of a patient to the duodenal papilla. From a proximal end side of the insertion portion of the endoscope, a treatment instrument is then inserted, whereby the treatment instrument is allowed to protrude from a distal end of the insertion portion of the endoscope. In the course of this insertion, an insertion portion of the treatment instrument is passively bent at multiple positions along a path from a manipulation portion to a treatment portion. In a conventional papillotome having a rotating function about an axis of a treatment portion, however, a knife portion may be oriented in a direction different from the 12 o'clock marker as a result of passive bending at multiple positions as mentioned hereinbefore because of the involvement of a rotational torque based on which a rotational manipulation at the manipulation portion can be transmitted to a distal end of the knife portion. If this becomes the case, a complicated manipulation will be needed to bring the direction of the knife portion into alignment with an intended direction.

BRIEF SUMMARY OF EMBODIMENTS

The disclosed technology has been made in view of the problem described hereinbefore.

One aspect of the disclosed technology is directed to a treatment instrument for use with an endoscope having a bendable portion with a channel for receiving the treatment instrument. An elevator is configured to raise the treatment instrument while being inserted in the channel for insertion of the treatment instrument. The treatment instrument comprises a sheath main body having opposed respective distal and proximal end regions along a longitudinal axis. The sheath main body includes an outer diameter such that the sheath main body capable of being fit into the channel for insertion of the treatment instrument of the endoscope. The sheath main body includes a lumen extending along the longitudinal axis in the distal end region. A wire-shaped incising portion is configured to engage with the sheath main body so as to protrude from an outer circumferential surface of the sheath main body in the distal end region and extending along the longitudinal axis of the sheath main body. The wire-shaped incising portion is used to incise a tissue. A wire is attached to at least a portion of the sheath main body, inserted in the lumen, and having a region in which the wire has different bending resistances when bent in two directions along two planes intersecting one another at right angles on a central axis of the sheath main body. When a plane that extends on the longitudinal axis of the sheath main body is accepted to be a reference plane of the sheath main body in which the incising portion protrudes from the outer circumferential surface of the sheath main body on the reference plane or in a direction tilted with respect to the reference plane, the wire is attached to the distal end region of the sheath main body in a state that one of the two planes in the region of the wire, the one plane extending along the direction in which the wire has a smaller bending resistance, is parallel to or coincident with the reference plane. The wire is configured to be rotatable with respect to the proximal end region of the sheath main body.

Another aspect of the disclosed technology is directed to an endoscope system used with a treatment instrument that comprises an endoscope having a bendable portion with a channel formed therethrough for receiving the treatment instrument. An elevator is configured to raise the treatment instrument while being inserted in the channel for insertion of the treatment instrument. An observation optical system is incorporated with the endoscope. The treatment instrument is configured to protrude from the channel to treat a treatment target. The treatment instrument includes a sheath main body having opposed respective distal and proximal end regions along a longitudinal axis. The sheath main body includes an outer diameter such that the sheath main body capable of being fit into the channel for insertion of the treatment instrument of the endoscope. The sheath main body includes a lumen extending along the longitudinal axis in the distal end region. A wire-shaped incising portion is configured to engage with the sheath main body so as to protrude from an outer circumferential surface of the sheath main body in the distal end region and extending along the longitudinal axis of the sheath main body. The wire-shaped incising portion is used to incise a tissue. A wire is attached to at least a portion of the sheath main body, inserted in the lumen, and having a region in which the wire has different bending resistances when bent in two directions along two planes intersecting one another at right angles on a central axis of the sheath main body. When a plane that extends on the longitudinal axis of the sheath main body being assumed to be a reference plane of the sheath main body in which the incising portion protrudes from the outer circumferential surface of the sheath main body on the reference plane or in a direction tilted with respect to the reference plane. The wire is attached to the distal end region of the sheath main body in a state that one of the two planes in the region of the wire, the one plane extending along the direction in which the wire has a smaller bending resistance, is parallel to or coincident with the reference plane. The wire is configured to be rotatable with respect to the proximal end region of the sheath main body and the sheath main body is positioned in the channel in a direction in which the sheath main body is bent at a distal end portion thereof by the elevator, and in which both the sheath main body and the reference plane are parallel to one another.

A further aspect of the disclosed technology is directed to a method of using a treatment instrument for incising a tissue. The treatment instrument includes a sheath main body having a lumen extends along a longitudinal axis thereof. A wire-shaped incising portion is configured to extend from an outer circumferential surface of the sheath main body so as to incise the tissue. A wire is attached to at least a portion of the sheath main body, inserted in the lumen, and having a region in which the wire has different bending resistances when bent in two directions along two planes intersecting each other at right angles on a central axis of the sheath main body. When a plane that extends on the longitudinal axis of the sheath main body is assumed to be a reference plane of the sheath main body, the incising portion protrudes, from the outer circumferential surface of the sheath main body, on the reference plane or in a direction tilted with respect to the reference plane and the wire is attached to at least a portion of the sheath main body in a state that one of the two planes in the region of the wire, the one plane extending along the direction in which the wire has a smaller bending resistance, is parallel to or coincident with the reference plane. The method comprises using an endoscope having a bendable portion including a channel for receiving the treatment instrument into a body wherein the channel being bendable by a bending movement of the bendable portion inside the body, inserting the sheath main body into the channel bent in the bendable portion, whereby the sheath main body is rotated together with the wire about the longitudinal axis, inducing the sheath main body to protrude from the channel at a distal end thereof while maintaining the incising portion in a direction tilted at an acute angle with respect to the reference plane, inserting into a duodenal papilla the distal end of the sheath main body that being protruded from the channel, and incising the duodenal papilla with the incising portion in a state that the sheath main body is inserted into the duodenal papilla.

BRIEF DESCRIPTION OF THE DRAWINGS

The technology disclosed herein, in accordance with one or more various embodiments, is described in detail with reference to the following figures. The drawings are provided for purposes of illustration only and merely depict typical or example embodiments of the disclosed technology. These drawings are provided to facilitate the reader's understanding of the disclosed technology and shall not be considered limiting of the breadth, scope, or applicability thereof. It should be noted that for clarity and ease of illustration these drawings are not necessarily made to scale.

DETAILED DESCRIPTION OF THE EMBODIMENTS

In the following description, various embodiments of the technology will be described. For purposes of explanation, specific configurations and details are set forth in order to provide a thorough understanding of the embodiments. However, it will also be apparent to one skilled in the art that the technology disclosed herein may be practiced without the specific details. Furthermore, well-known features may be omitted or simplified in order not to obscure the embodiment being described.

The disclosed technology has as objects thereof provision of a treatment instrument which, while having a function to adjust a direction of a treatment portion about an axis thereof, enables protrusion of a treatment portion in a predetermined direction about the axis when a sheath inserted in a treatment instrument insertion channel of an endoscope is caused to protrude at a distal end portion thereof in a bent state by an elevator, and also an endoscope system including the treatment instrument.

Referring to FIGS. 1 through 17, an embodiment of a high-frequency treatment instrument and an endoscope system according to the disclosed technology will hereinafter be described taking a papillotome as the high-frequency treatment instrument.

Figure 1:
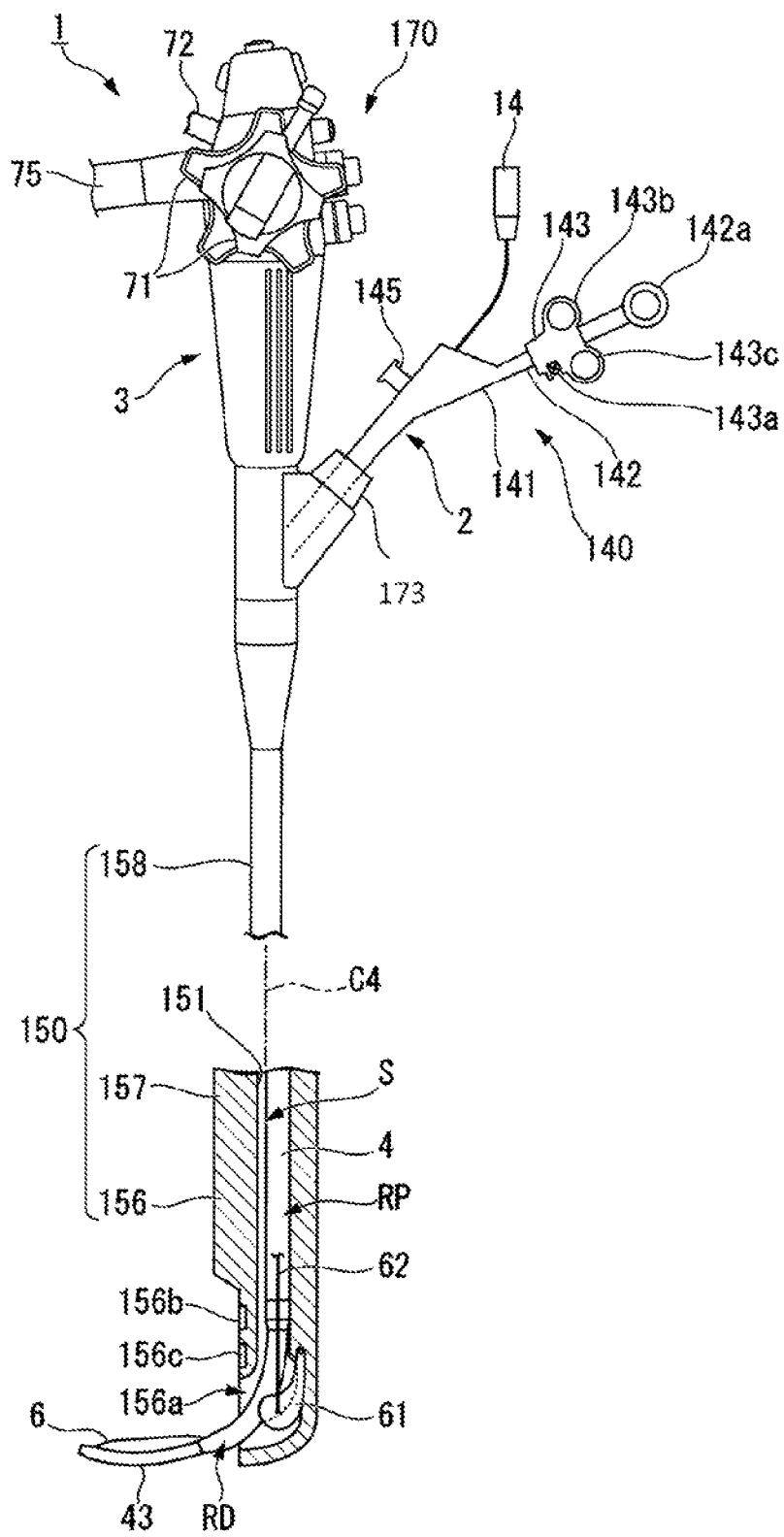
FIG. 1 is a view illustrating an endoscope system using a high-frequency treatment instrument according to an embodiment of the disclosed technology, and is a view illustrating a part thereof in cross-section.
Figure 2:
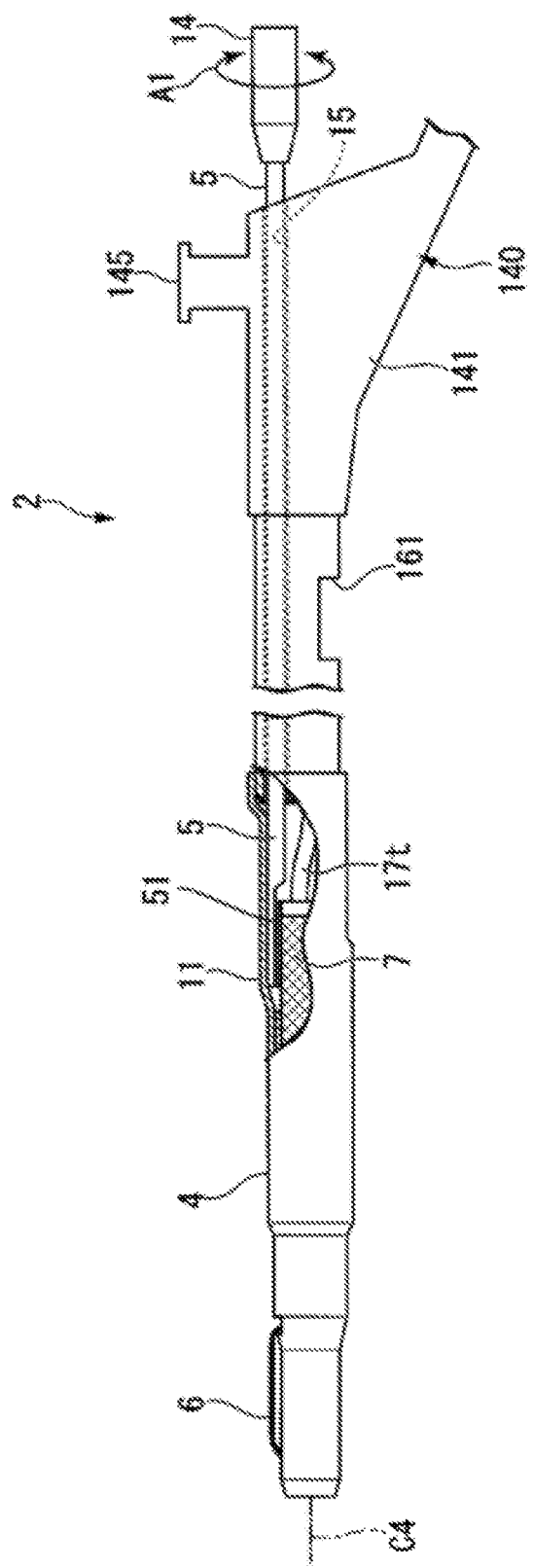
FIG. 2 is a side view of the high-frequency treatment instrument according to the embodiment of the disclosed technology, and is a view illustrating the high-frequency treatment instrument with a part thereof cut away.
Figure 3:
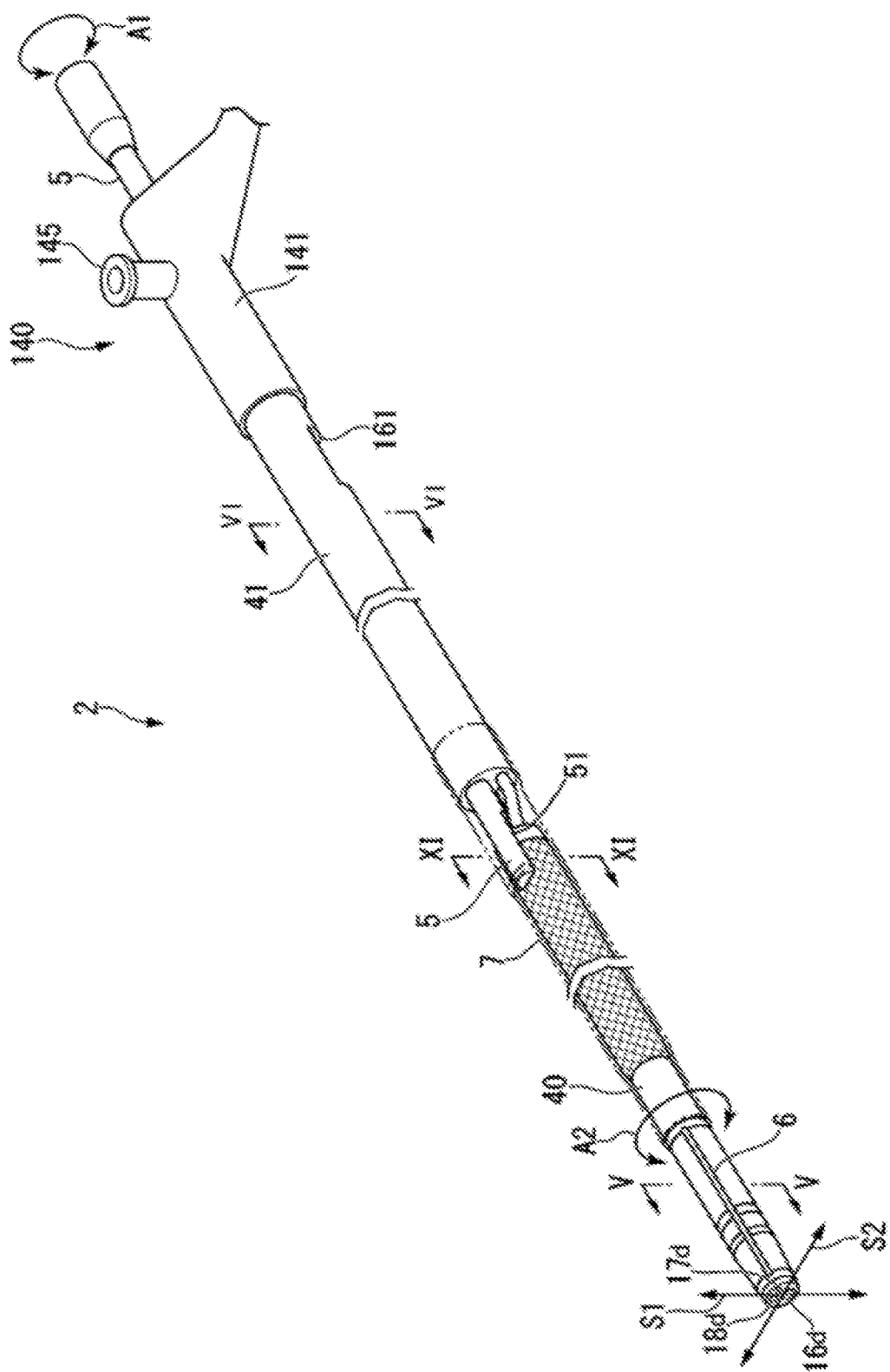
FIG. 3 is a perspective view of the high-frequency treatment instrument according to the embodiment of the disclosed technology, and is a view also illustrating a part of an internal structure thereof.
Figure 4:
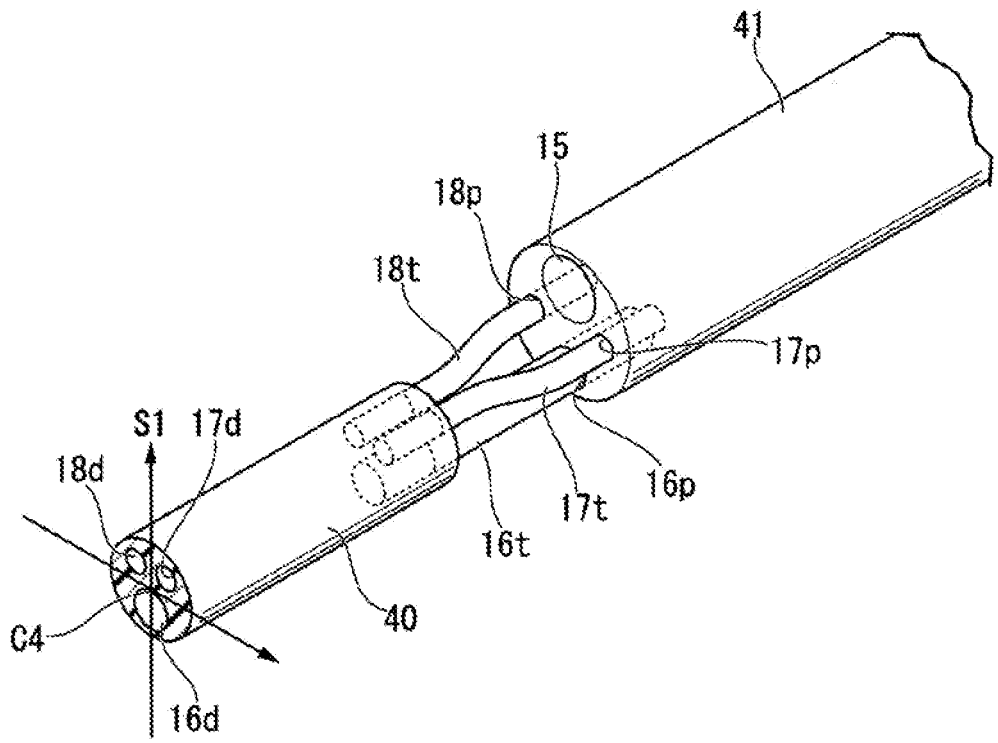
FIG. 4 is a perspective view illustrating a part of the high-frequency treatment instrument according to the embodiment of the disclosed technology.

FIG. 1 is a view illustrating an endoscope system 1 using a papillotome 2 according to the embodiment of the disclosed technology, and is a view illustrating a part of the papillotome 2 in cross-section. FIG. 2 is a side view of the papillotome 2 according to the embodiment, and is a view illustrating a part of the papillotome 2 in cross-section. FIG. 3 is a perspective view of the high-frequency treatment instrument, and is a view schematically illustrating a part of its internal structure. FIG. 4 is a perspective view illustrating a part of the high-frequency treatment instrument.

As illustrated in FIG. 1, the endoscope system 1 includes the papillotome 2, i.e., a treatment instrument or a high-frequency treatment instrument, and an endoscope 3. The papillotome 2 is used in combination with the endoscope 3.

As illustrated in FIGS. 1 and 2, the papillotome 2 includes a sheath main body 4, a torque wire 5, an incising portion 6, a handle 14, and a manipulation portion 140. In the following description, one end side of the papillotome 2, on which the handle 14 is disposed, will be called a "proximal end side," and an opposite end side of the papillotome 2, on which the incising portion 6 is disposed and which is to be inserted into the body, will be called a "distal end side." In the endoscope 3, one end side on which an endoscope manipulation portion 170 is disposed will also be called "the proximal end side," and an opposite end side which is to be inserted into a body and on which an imaging section of the endoscope 3 is disposed will also be called "the distal end side."

Further, in the following description, a plane which extends on a longitudinal axis C4 of the sheath main body 4 will be called a "reference plane S1 of the sheath main body." Furthermore, in the sheath main body 4, one of two regions with respect to an orthogonal plane S2, which intersects the reference plane S1 at right angles, as a boundary will be called a "first region R1," and the other region will be called a "second region R2."

The sheath main body 4 is an elongated member having a plurality of lumens along the longitudinal axis C4. The sheath main body 4 has a distal end region and a proximal end region, and has an outer diameter that enables its insertion into a treatment instrument insertion channel, i.e., a channel for insertion of a treatment instrument, of the endoscope. As illustrated in FIGS. 3 and 4, the sheath main body 4 has a distal end sheath 40, a proximal end sheath 41, and a plurality of connecting tubes 16t, 17t, and 18t. The sheath main body 4 is formed with a resin such as PTFE (polytetrafluoroethylene).

The distal end sheath 40 is a multi-lumen tube, which has a guide wire lumen 16d, a knife lumen 17d, and a fluid supply lumen 18d. The guide wire lumen 16d, the knife lumen 17d, and the fluid supply lumen 18d are formed extending along the longitudinal axis C4 from a distal end to a proximal end of the distal end sheath 40, and each open in the distal end and the proximal end of the distal end sheath 40.

In an outer circumferential surface of a distal end portion of the distal end sheath 40, two through-holes 17a and 17b are formed at an interval therebetween in the direction of the longitudinal axis C4. These through-holes 17a and 17b communicate the knife lumen 17d and an outer circumference of the distal end sheath 40 to one another. The through-holes 17a and 17b are formed along a direction tilted with respect to the reference plane S1 from an inner circumferential surface of the knife lumen 17d toward the outer circumferential surface of the distal end sheath 40.

On the proximal end portion of the distal end sheath 40, a braid 7 is externally fitted. The braid 7 is attached on the distal end sheath 40 with an adhesive, a heat shrink tube or the like. Employed as the braid 7 is, for example, a member obtained by bundling a plurality of thin stainless steel threads and braiding the resulting bundle into a lattice pattern to form a tubular shape, by winding one or more stainless steel threads or bands into a single-thread or multi-thread coil to form a tubular shape, or by winding single-thread or multi-thread coils, with the winding direction alternately changed, into multiple layers to form a tubular shape.

The distal end sheath 40 may include a pre-curved portion 43. The pre-curved portion 43 has a restoring force into a bent shape that the distal end sheath 40 is bent along the reference plane S1. The pre-curved portion 43 is bent so that the outer circumferential surface, in which the through-holes 17a and 17b are formed, is located on an inner side of the bent.

The proximal end sheath 41 is a multi-lumen tube, which has a guide wire lumen 16p, a knife lumen 17p, a fluid supply lumen 18p, and a torque wire lumen 15. The guide wire lumen 16p, the knife lumen 17p, the fluid supply lumen 18p, and the torque wire lumen 15 extend along the longitudinal axis C4 from a distal end to a proximal end of the proximal end sheath 41, and each open in the distal end and proximal end of the proximal end sheath 41.

Figure 6:
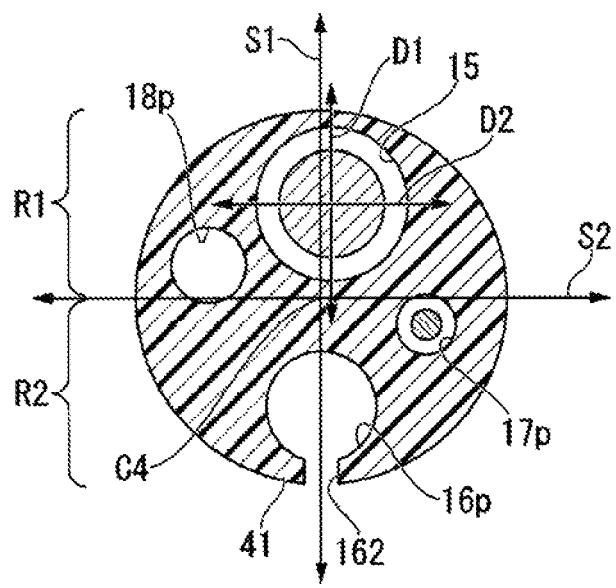
FIG. 6 is a cross-sectional view along line VI-VI of FIG. 3.

In the proximal end sheath 41, a slit 162, as depicted in FIG. 6, is formed along the longitudinal axis C4 in an outer circumferential surface of the proximal end sheath 41. In a proximal end portion of the proximal end sheath 41, an opening portion 161 is formed. This opening portion 161 is connected to the slit 162, and opens greater than the slit 162. The guide wire lumen 16p in the proximal end sheath 41 communicates to an outside of the proximal end sheath 41 via the slit 162 and the opening portion 161.

The distal end sheath 40 and the proximal end sheath 41 are arranged in series at an interval therebetween in the direction of the longitudinal axis C4. Between the proximal end sheath 40 and the distal end sheath 41, the connecting tubes 16t, 17t, and 18t are disposed. These connecting tubes 16t, 17t, and 18t connect the guide wire lumen 16d, and the knife lumen 17d, and the fluid supply lumen 18d in the distal end sheath 40 and the guide wire lumen 16p, the knife lumen 17p and the fluid supply lumen 18p in the proximal end sheath 41, respectively.

Figure 5:
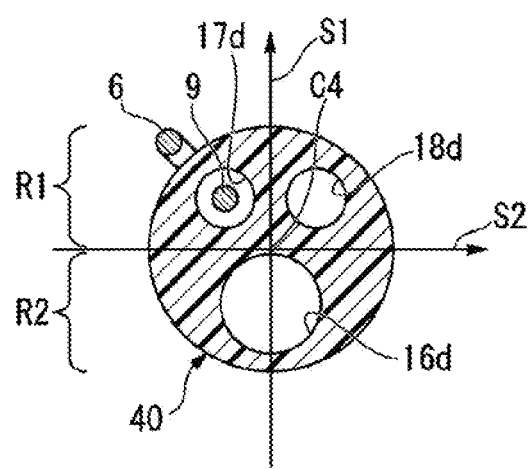
FIG. 5 is a cross-sectional view along line V-V of FIG. 3.

A description will next be made about the arrangement of the individual lumens in the distal end sheath 40 and the proximal end sheath 41. FIG. 5 is a cross-sectional view along line V-V of FIG. 3. FIG. 6 is a cross-sectional view along line VI-VI of FIG. 3. In each of FIGS. 5 and 6, the reference plane S1 is illustrated as a plane that extends in the up-and-down direction of the figure. In each of FIGS. and 6, the region above the orthogonal plane S2 is the first region R1, while the region below the orthogonal plane S2 is the second region R2.

As illustrated in FIG. 5, in the distal end sheath 40, the guide wire lumen 16d is formed in the second region R2 above the reference plane S1. In the distal end sheath 40, the guide wire lumen 16d is required to be located on the reference plane S1. The knife lumen 17d and the fluid supply lumen 18d are formed in the first region R1. The knife lumen 17d and the fluid supply lumen 18 are formed at positions with the reference plane S1 interposed therebetween. The knife lumen 17d is arranged on a left side of the reference plane S1 in a cross-section of the distal end sheath 40, the cross-section intersecting the longitudinal axis C4 at right angles, as viewed from the proximal end side.

As illustrated in FIG. 6, in the proximal end sheath 41, the slit 162 and the opening portion are formed on the reference plane S1. The guide wire lumen 16p is formed in the second region R2 on the reference plane S1. The torque wire lumen 15 is formed at a position that is in the first region R1 and includes the reference plane S1. The torque wire lumen 15 is preferably formed so that its center is located on or in the vicinity of the reference plane S1. The knife lumen 17p and the fluid supply lumen 18p are formed at positions in the vicinity of the orthogonal plane S2 with the reference plane S1 interposed therebetween.

The guide wire lumen 16p and the torque wire lumen 15 have internal diameters greater than those of the knife lumen 17p and the fluid supply lumen 18p. Further, the guide wire lumen 16p and the torque wire lumen 15 are preferably located on or in the vicinity of the reference plane S1. In the proximal end sheath 41, the locations of the knife lumen 17p and the fluid supply lumen 18p are not particularly limited, and are required to be formed off from the guide wire lumen 16p and the torque wire lumen 15.

As illustrated in FIG. 4, the guide wire lumen 16p in the distal end sheath 40 and the guide wire lumen 16d in the proximal end sheath 41 are connected and communicated to each other by a connecting tube 16t. The knife lumen 17d in the distal end sheath 40 and the knife lumen 17p in the proximal end sheath 41 are connected and communicated to each other by a connecting tube 17t. The fluid supply lumen 18d in the distal end sheath 40 and the fluid supply lumen 18p in the proximal end sheath 41 are connected and communicated to each other by the connecting tube 18t.

As illustrated in FIGS. 5 and 6, the distal end sheath 40 and the proximal end sheath 41 are different in the locations of the knife lumens 17p and 17d and also in the locations of the fluid supply lumens 18p and 18d. As illustrated in FIG. 4, the knife lumens 17p and 17d and the fluid supply lumens 18p and 18d form paths gently bent at the parts of the connecting tubes 17t and 18t.

Figure 17:
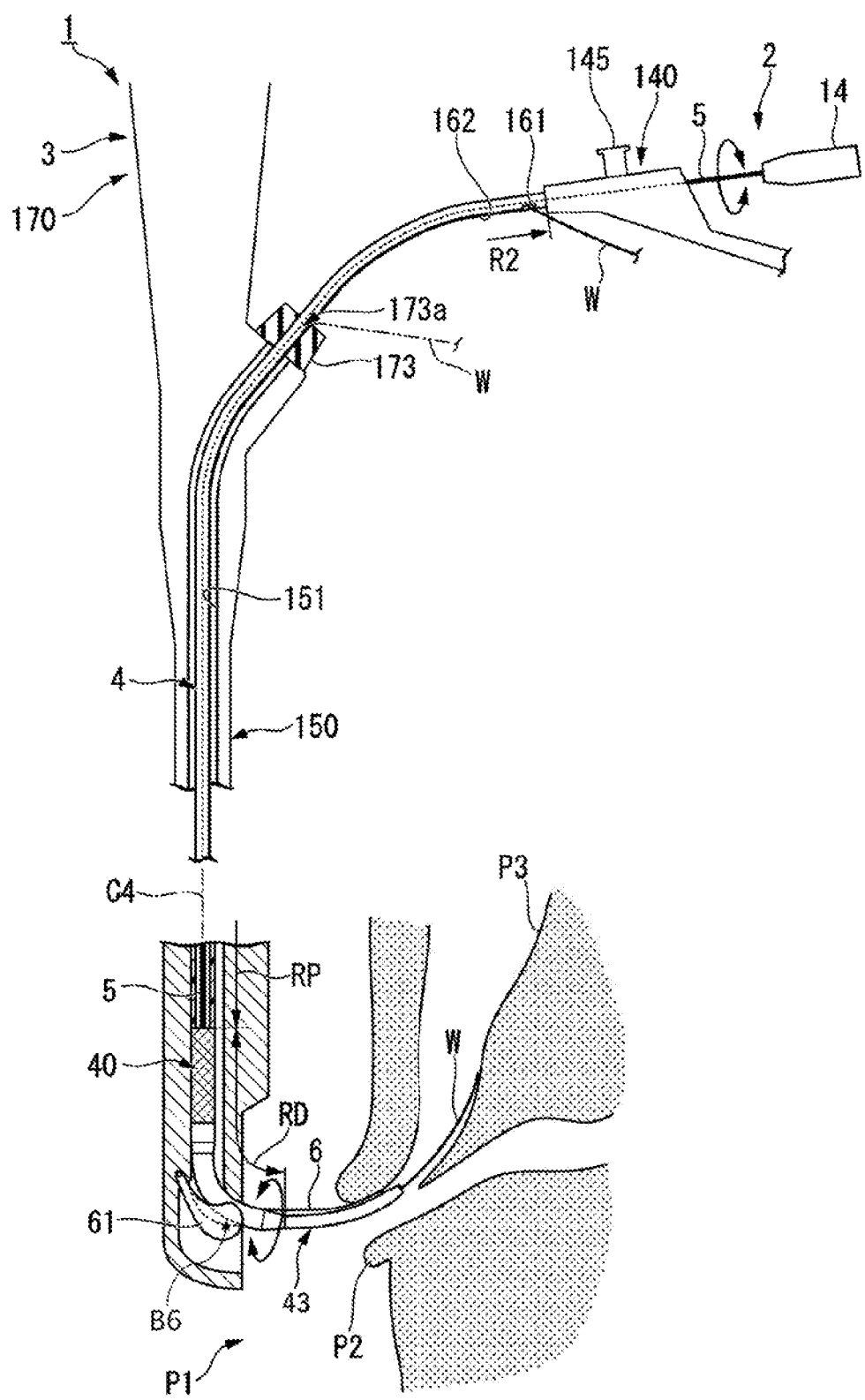
FIG. 17 is a schematic view illustrating a use example of the high-frequency treatment instrument according to the embodiment of the disclosed technology.

A guide wire W, as depicted in FIG. 17, is to be inserted through the guide wire lumen 16p.

Figure 7:
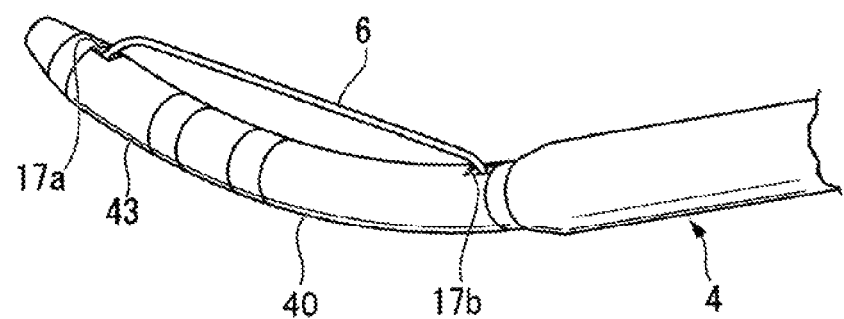
FIG. 7 is a perspective view illustrating an incising portion of the high-frequency treatment instrument according to the embodiment of the disclosed technology.

A conductive wire 9 is inserted through the knife lumens 17p and 17d. The conductive wire 9 is formed of a core wire having conductivity and an unillustrated insulating coating formed from an appropriate synthetic resin. FIG. 7 is a perspective view illustrating the incising portion 6 in this embodiment. The conductive wire 9 extends from the knife lumen 17d to an outside of the sheath main body 4 at the through-hole 17b on the proximal end side, is disposed extending along the longitudinal axis C4 toward the distal end side, enters the knife lumen 17d from the through-hole 17a on the distal end side, and is attached at a distal end thereof in the knife lumen 17d. A portion of the conductive wire 9, the portion being exposed from the through-holes 17a and 17b to the outside of the sheath main body 4, is not covered with the insulating coating, so that the core wire is exposed to configure the wire-shaped incising portion 6 that can incise a tissue.

The incising portion 6 protrudes to the outside of the sheath main body 4 from the through-hole 17a to the through-hole 17b. Accordingly, the incising portion 6 protrudes from an outer circumferential surface of the sheath main body 4 along a direction tilted at an acute angle with respect to the reference plane S1.

The torque wire 5 is a single-strand wire. As the torque wire 5 in this embodiment, the single-strand wire is illustrated. However, the torque wire 5 may be a wire formed by bundling a plurality of element wires, or a like wire. The torque wire 5 can be formed, for example, with stainless steel or a nickel-titanium alloy.

The torque wire 5 has, in at least a portion thereof, an anisotropic resistance region R5 in which the torque wire 5 has different bending resistances when bent in two directions along two planes D1 and D2 intersecting each other at right angles on a central axis C5. As illustrated in FIG. 6, the anisotropic resistance region R5 is different in bending resistance when the torque wire 5 is bent in the two directions that pass through the central axis C5 of the torque wire 5 and intersect each other at right angles. The plane that extends in one of the mutually orthogonal two directions, in which one direction the bending resistance is smaller, will be called a "first plane D1," and the plane that intersects the first plane D1 at right angles will be called a "second plane D2."

In this embodiment, the anisotropic resistance region R5 is formed over a predetermined region from a distal end of the torque wire 5 toward the proximal end side. Specifically, the anisotropic resistance region R5 has a proximal end formed extending to a position equal to the location of a distal end of an opening portion 161, which will be described hereinafter, in the direction of the longitudinal axis C4 of the sheath main body 4. The anisotropic resistance region R5 is only required to be included over at least a portion of the torque wire 5, but may be included over the entire length of the torque wire 5. If the anisotropic resistance region R5 is included over at least the portion of the torque wire 5, its formation in a region including a distal end portion of the torque wire 5 is preferred because a bending direction of the sheath main body 4 is restricted to a desired direction at a portion of the sheath main body 4, where the sheath main body 4 is connected to the braid 7 to be described hereinafter, and therefore accuracy of transmission of a rotational torque to a distal end region RD can be increased to permit adjusting the direction of the incising portion 6 with higher accuracy about the longitudinal axis C4.

The torque wire 5 extends at the central axis C5 thereof along the longitudinal axis C4 of the sheath main body 4, and is inserted in the torque wire lumen 15. The distal end of the torque wire 5 extends toward the distal end side beyond a distal end of the proximal end sheath 41, and is attached to the proximal end of the distal end sheath 40.

As illustrated in FIGS. 2 and 3, the distal end portion of the torque wire 5 has a semi-circular, cross-sectional shape intersecting the central axis C5 at right angles, and includes a planar portion 51 formed in a direction along the second plane D2. The distal end portion of the torque wire 5 is formed by a method that forms the distal end portion by cutting or compression deformation to have the cross-sectional shape described hereinbefore, by a method that welds a semi-circular wire to the distal end of the torque wire 5, or by a like method.

Figure 11:
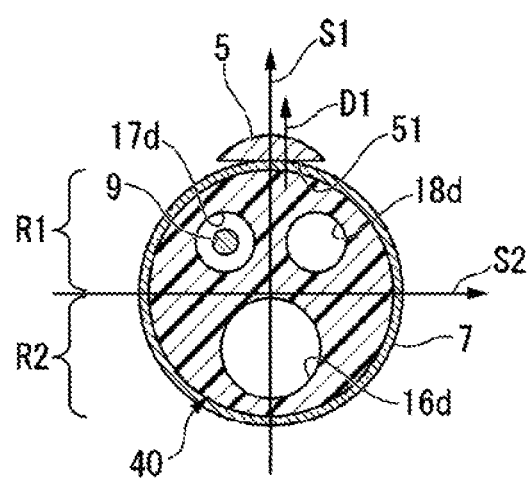
FIG. 11 is a cross-sectional view along line XI-XI of FIG. 3.
Figure 12:
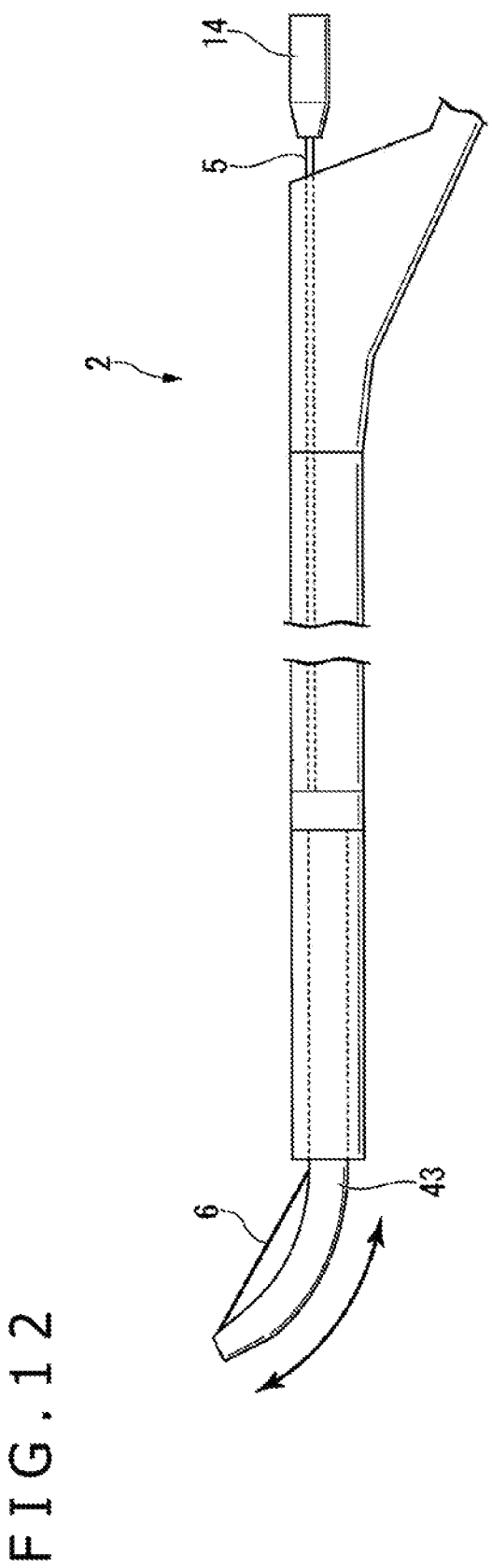
FIG. 12 is a side view illustrating an outline of the high-frequency treatment instrument according to the embodiment of the disclosed technology.

FIG. 11 is a cross-sectional view along line XI-XI of FIG. 3. As illustrated in FIG. 11, the distal end portion of the torque wire 5 is arranged so that the planar portion 51 lies in parallel to the orthogonal plane S2, and is attached to the braid 7 on the proximal end portion of the distal end sheath 40. The torque wire 5 is attached on the distal end sheath 40 with the first plane D1 in the anisotropic resistance region of the torque wire 5 being arranged to be parallel or coincident with the reference plane S1 as illustrated in FIG. 11.

Further, the torque wire 5 has the anisotropic resistance region R5 having different bending resistances when bent along the two planes intersecting each other at right angles on the central axis C5 of the torque wire 5. The torque wire 5 is attached on the distal end sheath 40 in a state that the first plane D1, along which the bending resistance is lower, out of the two planes intersecting each other at right angles on the central axis C5, extends along the reference plane S1 and the incising portion 6 is hence oriented at 11 o'clock marker on an endoscopic image when the distal end portion of the sheath main body 4, the distal end portion including the incising portion 6, is simply caused to protrude from a treatment instrument insertion channel 151. Preferably, the torque wire 5 is attached to the distal end sheath 40 so that the bent direction of the pre-curved portion 43 and the first plane D1 of the torque wire 5 extend in parallel to each other.

Figure 8:
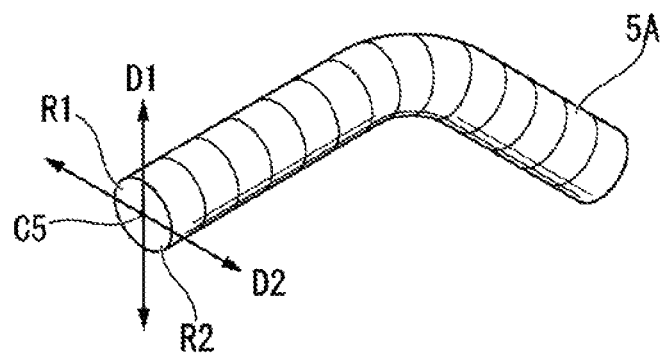
FIG. 8 is a schematic view illustrating a first configuration example of a torque wire.
Figure 9:
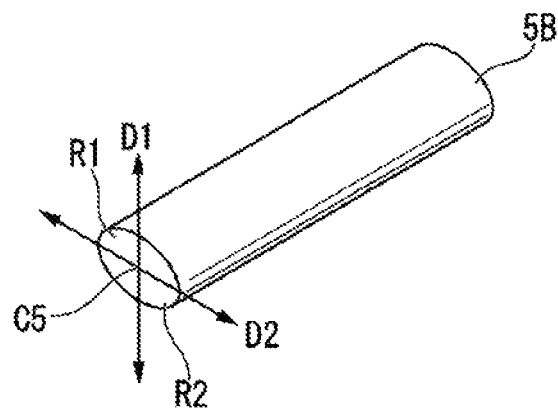
FIG. 9 is a schematic view illustrating a second configuration example of the torque wire.
Figure 10:
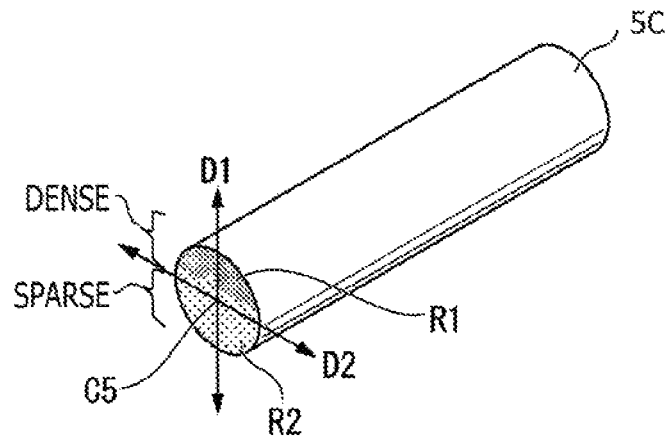
FIG. 10 is a schematic view illustrating a third configuration example of the torque wire.

Configuration examples of the torque wire 5 having the anisotropic resistance region R5 will be described hereinafter. FIGS. 8 to 10 are schematic views illustrating the first configuration example to the third configuration example of the torque wire 5.

A torque wire 5A of the first configuration example illustrated in FIG. 8 has a predetermined bending tendency imparted thereto. By imparting the bending tendency so that the torque wire 5A bends along a first plane D1 out of two planes intersecting each other at right angles on a central axis C5 of the torque wire 5A, the torque wire 5A is easy to bend along the first plane D1. An anisotropic resistance region is therefore formed with a bending resistance lower along the first plane D1 than along a second plane D2.

A torque wire 5B of the second configuration example of FIG. 9 is configured so that a cross-sectional shape orthogonal to a central axis C5 of the torque wire 5B is non-true circular, in other words, the diameters in the directions along two planes D1 and D2 orthogonal to each other on the central axis C5 differ from each other. As a result, in the torque wire 5B of the second configuration example, the anisotropic resistance region R5 of the torque wire 5 acts as an anisotropic stiffness region in which bending stiffness is different between two directions along the two planes D1 and D2 orthogonal to each other on the central axis C5. Specifically, the anisotropic stiffness region in which the bending stiffness is lower in the direction along first plane D1 than in the direction along the second plane D2, i.e., the anisotropic resistance region, is formed by making the diameter of the torque wire 5B longer in the direction along the second plane D2 than in the direction along the first plane D1.

A torque wire 5C of the third configuration example illustrated in FIG. 10 is an example in which the torque wire 5 is configured of a wire formed by bundling a plurality of element wires. In a cross-section of the torque wire 5C of the third configuration example, the cross-section intersecting a central axis C5 at right angles, element wires are arranged at a low density in one of regions, and element wires are arranged at a high density in the other region. In other words, in a cross-section of the torque wire 5C, the cross-section intersecting the central axis C5 at right angles, element wires are arranged at a low density along one of two directions, which extend along two planes D1 and D2 orthogonal to each other, in the region on one side, and element wires are arranged at a high density in the region on the other side. As a result, the torque wire 5C is more difficult to bend in the region in which the element wires are arranged at the high density compared with the region in which the element wires are arranged at the low density. If the region with the element wires arranged sparsely and the region with the element wires arranged at the high density are arranged side by side in the direction along the first plane D1 in the torque wire 5C, the magnitude of bending resistance of the torque wire 5C hence differs in the direction along the first plane D1 so that the torque wire 5C is easier to bend with the region, in which the element wires are arranged sparsely, being located on an inner side of the bent. As described hereinbefore, the anisotropic resistance region of the torque wire 5 may be formed by making the density of element wires different.

Moreover, the anisotropic resistance region of the torque wire 5 may be formed by combining two or more of the first configuration example to the third configuration example described hereinbefore. For example, the torque wire 5 may be a torque wire formed from a wire in which a plurality of element wires is bundled with the element wires arranged at different densities as in the third configuration example and in which the diameter is different in orthogonal two directions as in the second configuration example. In addition, to a torque wire having different diameters in orthogonal two directions as in the second configuration example, an additional bending tendency may be imparted as in the first configuration example.

The papillotome 2 is arranged so that with the sheath main body 4 being arranged so as to position the longitudinal axis C4 on a straight line from the manipulation portion 140 to the distal end portion of the sheath main body 4, the first plane D1 of the torque wire 5 and the reference plane S1 of the sheath main body 4 are parallel to each other and the second plane D2 of the torque wire 5 and the orthogonal plane S2 of the sheath main body 4 are parallel to each other.

In the case of the torque wire 5A of the first configuration example, the anisotropic resistance region is formed with the bending resistance lower along the first plane D1 than along the second plane D2 as described hereinbefore, and moreover a difference arises in bending resistance when the torque wire 5A is bent along the first plane D1.

In this case, the torque wire 5A is attached on the sheath main body 4 so that the first plane D1 of the torque wire 5A is parallel to the reference plane S1 and the second plane D2 of the torque wire 5A is parallel to the orthogonal plane S2. Preferably, the torque wire 5A is fixed on the distal end sheath 40 in a state that the direction in which the bending resistance is lower when bent along the first plane D1, i.e., the inner side of the bent shape under the bending tendency, is oriented toward the guide wire lumen 16d in the reference plane S1. Adoption of this configuration facilitates to allow the proximal end sheath 41 to bend along the bent of the torque wire 5A under the bending tendency when the proximal end sheath 41 is bent. As a consequence, the incising portion 6 is facilitated to orient at the 11 o'clock marker on an endoscopic image by simply causing the distal end portion of the sheath main body 4, which includes the incising portion 6, to protrude from the treatment instrument insertion channel 151. Preferably, the torque wire 5A is attached on the distal end sheath 40 so that upon bending the torque wire 5A along the first plane D1, the direction in which the bending resistance is lower is oriented opposite to the direction of the pre-curve of the pre-curved portion 43.

In the case of the torque wire 5B of the second configuration example, the torque wire 5B is attached on the sheath main body 4 so that, of the two planes D1 and D2 in the anisotropic stiffness region R5 of the torque wire 5B, the first plane D1 along the direction in which the bending stiffness is lower is parallel to or coincident with the reference plane S1.

In the case of the torque wire 5C of the third configuration example, the magnitude of the bending resistance of the torque wire 5C is different in the direction along the first plane D1 as described hereinbefore. In this case, as in the first configuration example, the torque wire 5C is also fixed on the sheath main body 4 so that the first plane D1 of the torque wire 5C is parallel to the reference plane S1 and the second plane D2 of the torque wire 5C is parallel to the orthogonal plane S2. Preferably, the torque wire 5C is attached on the distal end sheath 40 in a state that the direction in which the bending resistance is lower when bent along the first plane D1, i.e., the region of the sparse element wire density, is oriented toward the guide wire lumen 16d in the reference plane S1. Adoption of this configuration facilitates to allow the proximal end sheath 41 to bend, with the region in which the element wires are arranged sparsely in the torque wire 5C being located on the inner side of the bent, when the proximal end sheath 41 is bent. As a consequence, the incising portion 6 is facilitated to orient at the 11 o'clock marker on an endoscopic image by simply causing the distal end portion of the sheath main body 4, which includes the incising portion 6, to protrude from the treatment instrument insertion channel 151. Preferably, the torque wire 5C is attached on the distal end sheath 40 so that, upon bending the torque wire 5C along the first plane D1, the direction in which the bending resistance is lower is oriented opposite to the direction of the pre-curve of the pre-curved portion 43.

As illustrated in FIG. 2, in the direction of the longitudinal axis C4 of the sheath main body 4, the region in which the torque wire 5 is arranged will be called a "proximal end region RP," while the region on the distal end side of the attached portion between the proximal end portion of the distal end sheath 40 and the distal end portion of the torque wire 5 will be called a "distal end region RD."

The handle 14 of a larger diameter than the torque wire 5 is attached on the proximal end of the torque wire 5. The torque wire 5 is simply inserted in the torque wire lumen 15, and is not connected to the proximal end sheath 41. The torque wire 5 is therefore inserted rotatably relative to the torque wire lumen 15 about the central axis C5 by a rotating manipulation of the handle 14 about the central axis C5 as indicated by an arrow A1 in FIGS. 2 and 3. On the other hand, the distal end of the torque wire 5 is attached on the distal end sheath 40 so that, when the handle 14 is rotationally manipulated about the central axis C5, i.e., in a direction of an arrow A1 indicated in FIG. 3, a rotational torque is transmitted via the torque wire 5 and the distal end sheath 40 can be rotated relative to the proximal end sheath 41 about the longitudinal axis C4, i.e., in a direction of an arrow A2 indicated in FIG. 3.

As illustrated in FIGS. 2 and 3, the distal end sheath 40 and the proximal end sheath 41 are connected together via the connecting tubes 16t, 17t, and 18t and the torque wire 5, and the region from the distal end portion of the distal end sheath 40 to the distal end portion of the proximal end sheath 41 is covered by a cover tube 11.

As illustrated in FIGS. 1 to 3, the manipulation portion 140 is disposed on the proximal end side of the proximal end sheath 41. As illustrated in FIG. 1, the manipulation portion 140 has a manipulation portion main body 141, a handle shaft 142, and a slider 143. The manipulation portion main body 141 is attached to the proximal end portion of the proximal end sheath 41. The handle shaft 142 is a rod-shaped member attached at a distal end thereof to the manipulation portion main body 141. The slider 143 is disposed slidably relative to the handle shaft 142.

On the manipulation portion main body 141, a fluid supply ferrule 145 is disposed in communication with the fluid supply lumen 18p. An unillustrated syringe can be detachably attached to the fluid supply ferrule 145.

A ring 142a is attached to a proximal end portion of the handle shaft 142. A terminal 143a electrically connected to the conductive wire 9 is disposed on the slider 143. The terminal 143a can be connected to an external high-frequency power source. A pair of rings 143b and 143c is attached to the slider 143 with the handle shaft 142 interposed therebetween.

By moving, i.e., pushing in, the slider 143 toward the distal end side relative to the handle shaft 142, the incising portion 6 can be made straight and at the same time can be brought into a state that the incising portion 6 extends along the outer circumferential surface of the distal end sheath 40. By moving, i.e., pulling back, the slider 143 toward the proximal end side relative to the handle shaft 142, the distal end sheath 40 is relatively bent so that the incising portion 6 can be brought into a taut state (see FIG. 12).

As illustrated in FIG. 1, it is possible to use, as the endoscope 3, a known endoscope of the side view type in which an endoscope manipulation portion 170 is disposed on a proximal end of an endoscope insertion portion 150. The endoscope insertion portion 150 includes a passively bendable portion 158, a bendable portion 157, and a hard distal end portion 156. The passively bendable portion 158 has flexibility to be passively bendable upon receipt of an external force. The endoscope insertion portion 150 has the treatment instrument insertion channel 151 that extends over the entire length of the endoscope insertion portion 150 in the direction of a longitudinal axis. The papillotome 2 is inserted through the treatment instrument insertion channel 151.

In the treatment instrument insertion channel 151, an elevator 61 is disposed in the vicinity of a distal end opening 156a of the hard distal end portion 156. A manipulation wire 62 is connected to a distal end portion of the elevator 61, and the manipulation wire 62 is connected at a proximal end portion thereof to the endoscope manipulation portion 170 through the endoscope insertion portion 150. The manipulation wire 62 is illustrated only in FIG. 1. The elevator 61 raises the papillotome 2 inserted in the treatment instrument insertion channel 151.

In an edge portion of the distal end opening 156a, an illumination portion 156b and an observation portion 156c formed from an unillustrated CCD or the like, i.e., an observation optical system are disposed in a state that they are exposed to the outside. The illumination portion 156b and observation portion 156c are connected to the endoscope manipulation portion 170 via unillustrated wiring.

A description will be made of a method that uses the papillotome 2.

Figure 13:
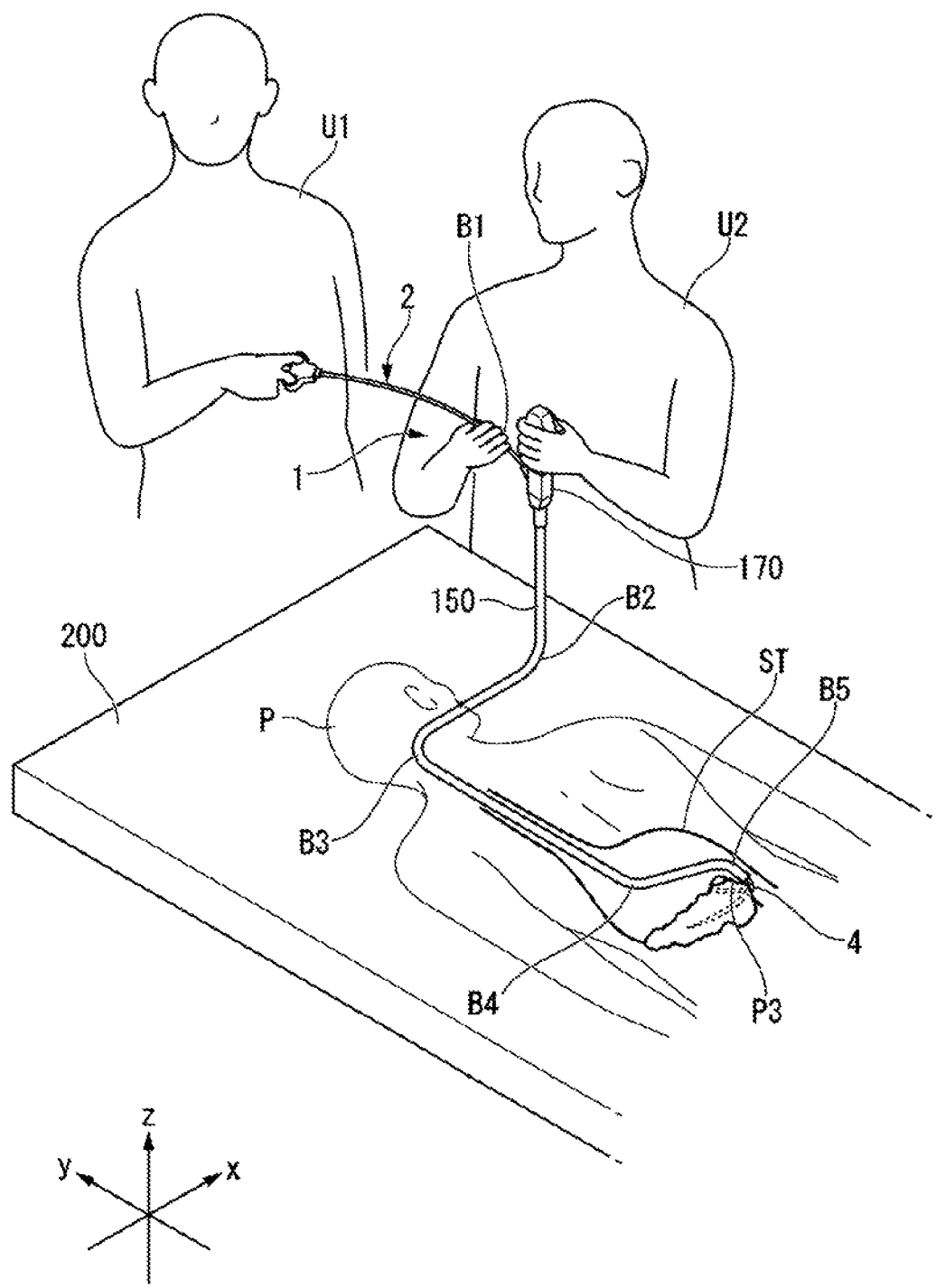
FIG. 13 is a schematic view illustrating a use example of an endoscope system according to the embodiment of the disclosed technology.

In the following method, a surgeon U2 and an assistant U1, who assists work by the surgeon U2, use the endoscope system 1 as users. The assistant U1 holds the manipulation portion 140 of the papillotome 2, and the surgeon U2 holds the endoscope manipulation portion 170 and a part of the sheath main body 4 of the papillotome 2. While checking an image displayed on a monitor and also manipulating the knob 171 to bend the bendable portion 157 as needed, the surgeon U2 inserts the endoscope insertion portion 150 of the endoscope 3 from a mouth of a patient P. At this time, the patient P lies in a prone position on an examination bed 200 with a face directed rightward as illustrated in FIG. 13.

The sheath main body 4 is inserted through a forceps plug 173, and is arranged so that the opening portion 161 is located on the proximal end side of the forceps plug 173.

As illustrated in FIG. 17, the guide wire W is inserted into the treatment instrument insertion channel 151 via a thorough-hole 173a of the forceps plug 173 of the endoscope 3. This guide wire W is introduced beforehand into the bile duct P3 through the duodenum P1.

The guide wire W is inserted at a proximal end portion thereof to a distal end of the guide wire lumen 16d of the papillotome 2, and is pulled out to the outside from the opening portion 161 of the sheath main body 4. The sheath main body 4 of the papillotome 2 is inserted into the treatment instrument insertion channel 151 via the through-hole 173a of the forceps plug 173.

When the sheath main body 4 is inserted through the forceps plug 173, a frictional force acts between an inner circumferential surface of the through-hole 173a of the forceps plug 173 and the sheath main body 4, so that the forceps plug 173 and the sheath main body 4 are sealed substantially water-tight.

Figure 14:
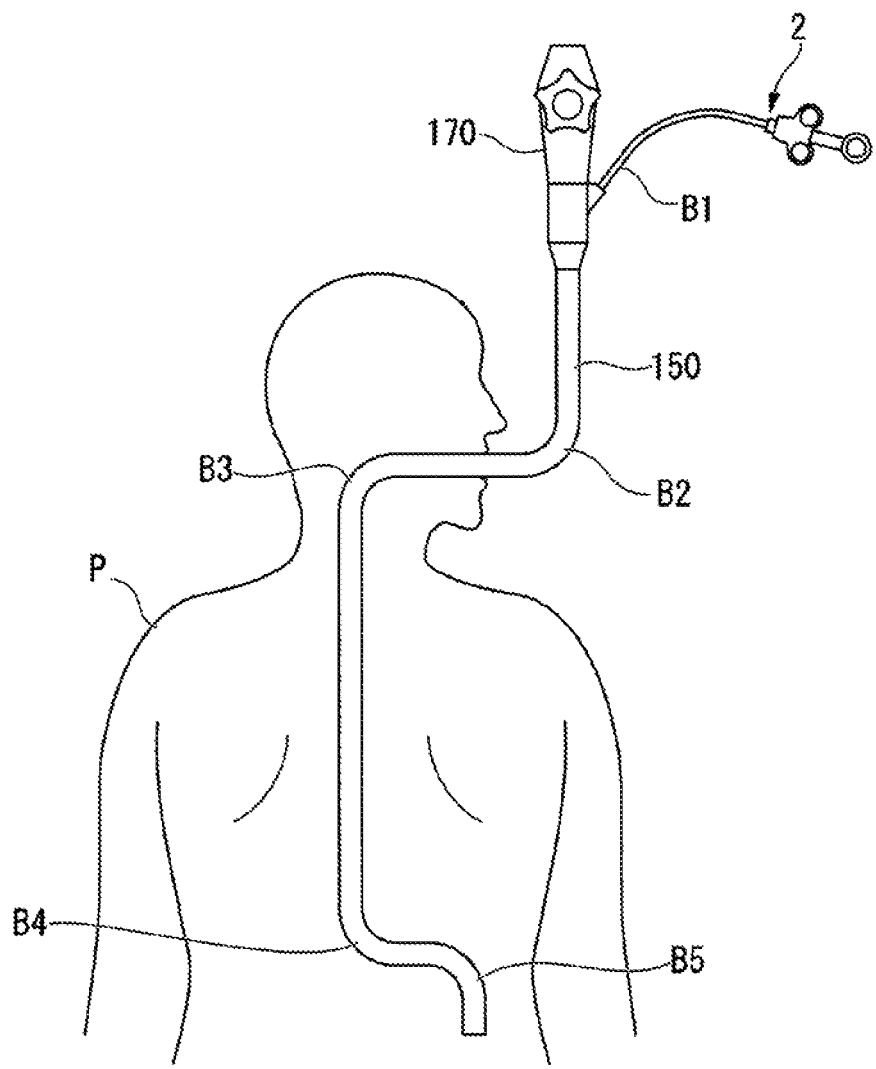
FIG. 14 is a schematic view illustrating a use example of the high-frequency treatment instrument according to the embodiment of the disclosed technology.
Figure 15:
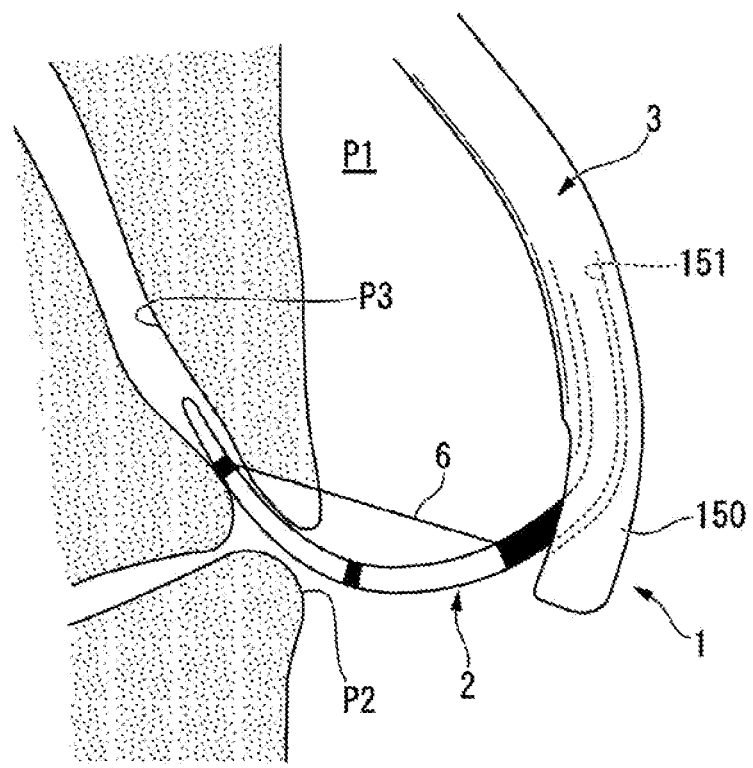
FIG. 15 is a schematic view illustrating another use example of the endoscope system according to the embodiment of the disclosed technology.

When the endoscope insertion portion 150 reaches near the bile duct P3 as a treatment target site from the mouth of the patient P, the sheath main body 4 of the papillotome 2 and the passively bendable portion 158 of the endoscope insertion portion 150 are bent at multiple locations. Specifically, they are bent at a first bent portion B1 to a sixth bent portion B6 as illustrated in FIGS. 13 and 14. The first bent portion B1 is a portion held by the surgeon U2 after the papillotome 2 was inserted into the forceps plug 173 of the endoscope 3. The second bent portion B2 is a portion bent toward the mouth of the patient P when the endoscope insertion portion 150 hanging downward from the position of the endoscope manipulation portion 170 held by the surgeon U2 has reached in the vicinity of an upper surface of the examination bed 200. The third bent portion B3 is a portion bent along the throat of the patient P. The fourth bent portion B4 and fifth bent portion B5 are portions bent when the sheath main body 4 and endoscope insertion portion 150 was passed through a stomach ST of the patient P. The sixth bent portion B6 is a portion bent when the distal end portion of the sheath main body 4 was raised by the elevator 61 of the endoscope 3.

Now, an upper surface of the examination bed 200 is assumed to be an x-y plane, and a direction vertical to the examination bed 200 is assumed to be a z-direction. The first bent portion B1 and the second bent portion B2 are each a bent having a component in the z-direction indicated in FIG. 13. The endoscope insertion portion 150 and sheath main body 4 on the distal end side as compared to the second bent portion B2 extend substantially in parallel to the upper surface, i.e., the x-y plane indicated in FIG. 13, of the examination bed 200. Accordingly, the third bent portion B3, the fourth bent portion B4 and, the fifth bent portion B5 of the endoscope insertion portion 150 are also bent along the x-y plane. At this time, the sheath main body 4 is passively bent under a force applied thereto by the bending of the endoscope insertion portion 150. The proximal end region RP of the sheath main body 4 is configured to facilitate bending along the reference plane S1. As a result, in a state that the proximal end sheath 41 is located at one of the third bent portion B3, the fourth bent portion B4 and, the fifth bent portion B5 of the endoscope insertion portion 150, at which bent portions B3, B4 and, B5 the proximal end region RP of the sheath main body 4 is located, the sheath main body 4 rotates about the longitudinal axis C4 in the treatment instrument insertion channel 151 so that the reference plane S1 lies substantially in parallel to the x-y plane. Consequently, owing to the configuration of the sheath main body 4 as described hereinbefore, the sheath main body 4 is allowed to protrude from the treatment instrument insertion channel 151 so that the distal end of the sheath main body 4 is oriented in a predetermined direction about the longitudinal axis C4. As a consequence, the sixth bent portion B6 can be easily oriented in a predetermined direction by the elevator 61.

The surgeon U2 adjusts the amount of insertion of the sheath main body 4 to be inserted into the treatment instrument insertion channel 151 of the endoscope 3, and causes the distal end of the sheath main body 4 to protrude from the treatment instrument insertion channel 151.

The torque wire 5 is attached to the proximal end sheath 40 so that the first plane D1 of the torque wire 5 lies in the bent direction of the pre-curved portion 43. Specifically, as presented in the first configuration example and third configuration example described hereinbefore, if there is a difference in bending resistance upon bending the torque wire 5 along the first plane D1, the torque wire 5 is attached on the distal end sheath 40 so that the direction in which the bending resistance is lower is oriented opposite to the direction of the pre-curve of the pre-curved portion 43. Owing to this configuration, the sheath main body 4 is configured to be easily bendable in an S-shape with the proximal end region RP and the distal end region RD bent in opposite directions when the sheath main body 4 is viewed along the orthogonal plane S2. By this configuration, the torque wire 5 is bent in the direction of the pre-curve of the pre-curved portion 43 of the sheath main body along the first plane D1, thereby facilitating insertion of the incising portion 6 into the duodenal papilla P2.

By configuring the papillotome 2 as described hereinbefore, in the path along which the sheath main body 4 is inserted through the treatment instrument insertion channel 151, the portion of the sheath main body 4 in which the incising portion 6 is located can be inserted along the fourth bent portion B4 and the fifth bent portion B5 bent along the curve of the stomach ST. At this time, the pre-curved portion 43 and the torque wire 5 are bent along the reference plane S1, so that the reference plane S1 is arranged to be located on a plane substantially parallel to the x-y plane of the examination bed 200 and the sheath main body 4 can be smoothly bent. Further, the distal end portion of the sheath main body 4 is bent by the elevator 61 on the reference plane S1. As a result, the distal end of the sheath main body 4 is allowed to protrude with the distal end portion of the sheath main body 4 being positioned so that the reference plane S1 lies substantially in the direction of the 12 o'clock marker in an endoscopic image. At this time, the distal end portion of the sheath main body 4 is allowed to protrude in a state that the incising portion 6, which protrudes in a direction tilted at an acute angle with respect to the reference plane S1, is oriented at the 11 o'clock marker.

Subsequently, the distal end of the sheath main body 4 is inserted into the duodenal papilla P2. If it is desired to bring the direction of the incising portion 6 into alignment with a target site of treatment, for example, at the junction of the bile duct and the pancreatic duct or a like site, the handle 14 is rotationally manipulated about the central axis C5 to adjust the direction of the incising portion 6.

Based on an image displayed on the monitor, the surgeon U2 checks the site of an encircling fold P4 to determine the incising direction, and also checks the current direction of the incising portion 6. Described specifically, the surgeon U2 determines the direction, in which an incision is to be made, to be the direction of the 12 o'clock mark indicated by an arrow E1 in FIG. 16, and rotationally manipulates the handle 14 about the central axis C5 to check the direction of the incision portion 6. If the distal end portion of the sheath main body 4 is bent by the elevator 61 at this time, the distal end of the sheath main body 4 is allowed to protrude with the reference plane S1 oriented to lie in the direction of the 12 o'clock marker indicated by an arrow E1 in FIG. 16 because the papillotome 2 includes the torque wire 5 having the anisotropic resistance region R5.

Figure 16:
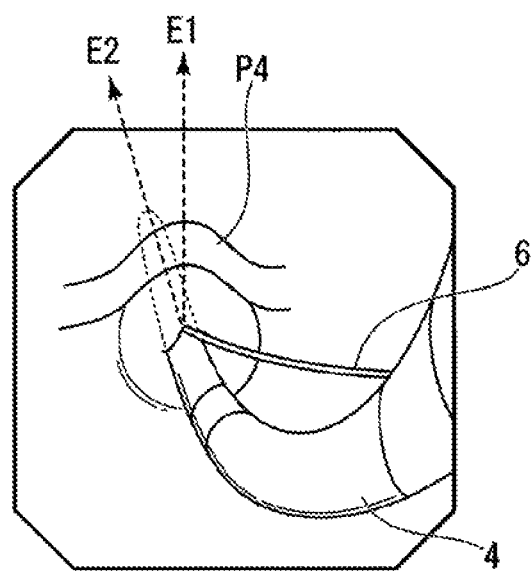
FIG. 16 is a schematic view illustrating an example of an endoscopic image at the time of use of the endoscope system according to the embodiment of the disclosed technology.

If the position of the encircling fold P4 of the patient P is offset from the direction of the 12 o'clock mark in the image displayed on the monitor, the surgeon U2 changes the direction of the incising portion 6 to the direction of the 11 o'clock mark, i.e., to a direction indicated by an arrow E2 in FIG. 16 as will be described hereinafter.

The surgeon U2 first manipulates the lever 72 to fully raise the elevator 61 to clamp the sheath main body 4 between the fully raised elevator 61 and an inner circumferential surface of the treatment instrument insertion channel 151.

The assistant U1 rotates the handle 14 about the longitudinal axis C4, whereby the torque wire 5 is rotated to one side in the circumferential direction on the proximal end side of the distal end sheath 40.

A rotational torque is transmitted to the braid 7 via the torque wire 5 inserted in the torque wire lumen 15 of the sheath main body 4, and is then transmitted to the distal end region RD. As a consequence, the rotational torque inputted by the assistant U1 at the manipulation portion 140 is transmitted to the distal end region RD of the sheath main body 4 via the torque wire 5, whereby the sheath main body 4 is rotated about the longitudinal axis C4.

As the distal end of the proximal end region RP is connected to the proximal end side of the distal end region RD, the rotational torque is also transmitted from the distal end region RD to the proximal end region RP at this time. The rotational torque applied to the distal end of the proximal end region RP is, however, absorbed through twisting of the sheath main body 4, because the sheath main body 4 is formed with a material that is lower in rotational torque transmission capability but higher in twistability than that of torque wire 5.

While rotating the handle 14 to cause a rotational torque to act on the sheath main body 4 via the torque wire 5 and observing the direction of the distal end portion of the sheath main body 4 about the longitudinal axis C4 on the image displayed on the monitor of the endoscope 3, the assistant U1 brings the direction of the incising portion 6 into alignment with the direction E2 of the 11 o'clock mark. As described hereinbefore, the direction of the incising portion 6 can be adjusted even if the direction, in which an incision is to be made, is different from the direction of the 12 o'clock mark due to an individual difference among patients.

When the direction of the incising portion 6 has then oriented in the desired direction, specifically has oriented at the direction E2 of the 11 o'clock mark, the handle 14 is rotated in the circumferential direction on the proximal end side of the torque wire 5 as illustrated in FIG. 2, whereby the rotational torque acting on the proximal end side of a portion 13 of the sheath main body 4 is cancelled out.

A lever 72 is next manipulated to lower the elevator 61. The terminal 143a of the papillotome 2 is connected to the high-frequency power source. The fingers are appropriately inserted into rings 42a, 43b, and 43c of the manipulation portion 140 to hold the manipulation portion 140, and the slider 143 is pulled back to make the incising portion 6 taut.

A high-frequency current is supplied from the high-frequency power source, and the lever 72 is manipulated to raise and lower the elevator 61 so that the distal end of the sheath main body 4 is caused to perform a swinging motion. To the tissue of the duodenal papilla P2 with which the incising portion 6 has been maintained in contact, the high-frequency current and a pressure produced by a tension of the incising portion 6 are applied so that the duodenal papilla P2 is incised. If a necessary length of incision is successfully confirmed to have reached based on an image on the monitor, for example, the supply of the high-frequency current is stopped.

After completion of the incision of the duodenal papilla P2, the slider 143 is pushed in to cause the incising portion 6 to lie along the distal end portion of the sheath main body 4, and the papillotome 2 is then pulled out. At this time, an unillustrated basket forceps or the like is inserted in place of the papillotome 2. The basket forceps is inserted from the incised duodenal papilla P2 into the bile duct P3 to capture stones. The stones are removed from the bile duct P3 after crushing if they are large or as they are if they are small. After the removal of the stones, the basket forceps and endoscope 3 are pulled out of the body.

The embodiment of the disclosed technology has hereinbefore been described in detail with reference to the drawings. However, the specific configuration of the disclosed technology is not limited to the embodiment, and includes modifications, combinations and the like of elements within a scope not departing from the spirit of the disclosed technology. Moreover, the individual features presented in the embodiment can obviously be used in appropriate combinations.

In the embodiment described hereinbefore, the three or four lumens are described to be formed in the sheath main body, for example. However, at least one lumen is required to be formed in the sheath main body.

The papillotome has been described as an example of the high-frequency treatment instrument, but the high-frequency treatment instrument is not limited to such a papillotome. Even in the case of a high-frequency treatment instrument with an L-shaped high-frequency knife disposed on the distal end of the sheath main body 4, for example, the high-frequency knife can be precisely oriented in a desired direction about the longitudinal axis C4 of the sheath main body 4.

In the embodiment described hereinbefore, the example with the pre-curved portion 43 included in the distal end sheath 40 is presented. However, the pre-curved portion is not an essential element in the disclosed technology. Further, the example, in which the pre-curved portion 43 is bent on the reference plane S1, is presented in the embodiment described hereinbefore. However, this is not an essential feature of the disclosed technology.

In the embodiment described hereinbefore, there is presented the example in which the incising portion 6 protrudes from the outer circumferential surface of the sheath main body 4 in the direction tilted with respect to the reference plane S1. However, the incising portion 6 may protrude from the outer circumferential surface of the sheath main body 4 in a direction along the reference plane S1.

In the embodiment described hereinbefore, there is presented the example in which the distal end portion of the sheath main body 4 is caused to protrude in the state that the incising portion 6 protruding in the direction inclined with respect to the reference plane S1 is oriented in the direction of the 11 o'clock mark, but the protruding direction of the incising portion 6 is not limited to the direction. The incising portion 6 is only required to be configured so that it protrudes from the outer circumferential surface of the sheath main body 4 in a direction tilted in a range of 45 degrees and smaller from the reference plane S1. Owing to this configuration, the direction of the incising portion 6 can be precisely adjusted during use by bringing the bent direction of the sheath main body 4 and the torque wire and the protruding direction of the incising portion 6 from the sheath main body 4 into alignment with each other via the reference plane S1.

According to the high-frequency treatment instrument and endoscope system of the embodiment, the distal end portion of the sheath main body inserted in the treatment instrument insertion channel of the endoscope is allowed to protrude precisely in a predetermined direction about its axis when the distal end portion of the sheath main body is caused to protrude in the state that the distal end portion of the sheath main body has been bent by the elevator.

In sum, one aspect of the disclosed technology is directed to a treatment instrument for use with an endoscope having a bendable portion with a channel for receiving the treatment instrument. An elevator is configured to raise the treatment instrument while being inserted in the channel for insertion of the treatment instrument. The treatment instrument comprises a sheath main body having opposed respective distal and proximal end regions along a longitudinal axis. The sheath main body includes an outer diameter such that the sheath main body capable of being fit into the channel for insertion of the treatment instrument of the endoscope. The sheath main body includes a lumen extending along the longitudinal axis in the distal end region. A wire-shaped incising portion is configured to engage with the sheath main body so as to protrude from an outer circumferential surface of the sheath main body in the distal end region and extending along the longitudinal axis of the sheath main body. The wire-shaped incising portion is used to incise a tissue. A wire is attached to at least a portion of the sheath main body, inserted in the lumen, and having a region in which the wire has different bending resistances when bent in two directions along two planes intersecting one another at right angles on a central axis of the sheath main body. When a plane that extends on the longitudinal axis of the sheath main body is accepted to be a reference plane of the sheath main body in which the incising portion protrudes from the outer circumferential surface of the sheath main body on the reference plane or in a direction tilted with respect to the reference plane, the wire is attached to the distal end region of the sheath main body in a state that one of the two planes in the region of the wire, the one plane extending along the direction in which the wire has a smaller bending resistance, is parallel to or coincident with the reference plane. The wire is configured to be rotatable with respect to the proximal end region of the sheath main body.

The region of the wire is an anisotropic resistance region in which the wire has different bending resistances in the two directions along the two planes intersecting each other at right angles on the central axis. The wire is attached to the sheath main body so that one of the two planes in the anisotropic resistance region of the wire, the one plane extending along the direction in which the wire has a lower bending stiffness, is parallel to or coincident with the reference plane. The wire is formed from a plurality of element wires and is configured to have the different bending resistances in the two directions along the two planes by arranging the element wires so that a region of a high element wire density and a region of a low element wire density are arranged side by side along the reference plane in the region of the wire. The wire is imparted with a bending tendency along one of the two directions, which extend along the two planes in the region, respectively. The incising portion is configured to protrude from the outer circumferential surface of the sheath main body in a direction tilted with respect to the reference plane in a range not greater than 45 degrees from the reference plane. The treatment instrument further comprises a braid that is attached on the distal end region so as to cover an outer circumference of the sheath main body and a handle that is attached to a proximal end of the wire. The wire is configured to be rotatable about the central axis in the lumen and is attached at a distal end thereof to the braid. The sheath main body includes a pre-curved portion having a restoring force into a bent shape that the sheath main body is bent at a central axis thereof on the reference plane in the distal end region thereof.

Another aspect of the disclosed technology is directed to an endoscope system used with a treatment instrument that comprises an endoscope having a bendable portion with a channel formed therethrough for receiving the treatment instrument. An elevator is configured to raise the treatment instrument while being inserted in the channel for insertion of the treatment instrument. An observation optical system is incorporated with the endoscope. The treatment instrument is configured to protrude from the channel to treat a treatment target. The treatment instrument includes a sheath main body having opposed respective distal and proximal end regions along a longitudinal axis. The sheath main body includes an outer diameter such that the sheath main body capable of being fit into the channel for insertion of the treatment instrument of the endoscope. The sheath main body includes a lumen extending along the longitudinal axis in the distal end region. A wire-shaped incising portion is configured to engage with the sheath main body so as to protrude from an outer circumferential surface of the sheath main body in the distal end region and extending along the longitudinal axis of the sheath main body. The wire-shaped incising portion is used to incise a tissue. A wire is attached to at least a portion of the sheath main body, inserted in the lumen, and having a region in which the wire has different bending resistances when bent in two directions along two planes intersecting one another at right angles on a central axis of the sheath main body. When a plane that extends on the longitudinal axis of the sheath main body being assumed to be a reference plane of the sheath main body in which the incising portion protrudes from the outer circumferential surface of the sheath main body on the reference plane or in a direction tilted with respect to the reference plane. The wire is attached to the distal end region of the sheath main body in a state that one of the two planes in the region of the wire, the one plane extending along the direction in which the wire has a smaller bending resistance, is parallel to or coincident with the reference plane. The wire is configured to be rotatable with respect to the proximal end region of the sheath main body and the sheath main body is positioned in the channel in a direction in which the sheath main body is bent at a distal end portion thereof by the elevator, and in which both the sheath main body and the reference plane are parallel to one another.

A further aspect of the disclosed technology is directed to a method of using a treatment instrument for incising a tissue. The treatment instrument includes a sheath main body having a lumen extends along a longitudinal axis thereof. A wire-shaped incising portion is configured to extend from an outer circumferential surface of the sheath main body so as to incise the tissue. A wire is attached to at least a portion of the sheath main body, inserted in the lumen, and having a region in which the wire has different bending resistances when bent in two directions along two planes intersecting each other at right angles on a central axis of the sheath main body. When a plane that extends on the longitudinal axis of the sheath main body is assumed to be a reference plane of the sheath main body, the incising portion protrudes, from the outer circumferential surface of the sheath main body, on the reference plane or in a direction tilted with respect to the reference plane and the wire is attached to at least a portion of the sheath main body in a state that one of the two planes in the region of the wire, the one plane extending along the direction in which the wire has a smaller bending resistance, is parallel to or coincident with the reference plane. The method comprises using an endoscope having a bendable portion including a channel for receiving the treatment instrument into a body wherein the channel being bendable by a bending movement of the bendable portion inside the body, inserting the sheath main body into the channel bent in the bendable portion, whereby the sheath main body is rotated together with the wire about the longitudinal axis, inducing the sheath main body to protrude from the channel at a distal end thereof while maintaining the incising portion in a direction tilted at an acute angle with respect to the reference plane, inserting into a duodenal papilla the distal end of the sheath main body that being protruded from the channel, and incising the duodenal papilla with the incising portion in a state that the sheath main body is inserted into the duodenal papilla.

The method further comprises an observation optical system being incorporated with the endoscope so as to permit a user to diagnose inside the body.

While various embodiments of the disclosed technology have been described above, it should be understood that they have been presented by way of example only, and not of limitation. Likewise, the various diagrams may depict an example schematic or other configuration for the disclosed technology, which is done to aid in understanding the features and functionality that can be included in the disclosed technology. The disclosed technology is not restricted to the illustrated example schematic or configurations, but the desired features can be implemented using a variety of alternative illustrations and configurations. Indeed, it will be apparent to one of skill in the art how alternative functional, logical or physical locations and configurations can be implemented to implement the desired features of the technology disclosed herein.

Although the disclosed technology is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the disclosed technology, whether or not such embodiments are described and whether or not such features are presented as being a part of a described embodiment. Thus, the breadth and scope of the technology disclosed herein should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent.

Additionally, the various embodiments set forth herein are described in terms of exemplary schematics, block diagrams, and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular configuration.

What is claimed is:

1. A treatment instrument for use with an endoscope including a bendable portion with a channel for receiving the treatment instrument, and an elevator configured to raise the treatment instrument while being inserted in the channel, the treatment instrument comprising:

a sheath main body including: opposed respective distal and proximal end regions along a longitudinal axis, an outer diameter such that the sheath main body is capable of being fit into the channel of the endoscope, and a lumen extending along the longitudinal axis, a wire-shaped incising portion that is configured to engage with the sheath main body so as to protrude from an outer circumferential surface of the sheath main body in the distal end region and extend along the longitudinal axis of the sheath main body, the wire-shaped incising portion being configured to incise a tissue, and a wire that:
is inserted in the lumen of the sheath main body,
includes a region in which the wire has different bending resistances when bent in two directions along two planes intersecting one another at right angles on a central axis of the wire, and
is attached to the distal end region of the sheath main body in a state that one plane of the two planes in the region of the wire is parallel to or coincident with a reference plane of the sheath main body, the reference plane extending along the longitudinal axis of the sheath main body, and the one plane extending along the direction in which the wire has a lower bending resistance, wherein
the incising portion protrudes from the outer circumferential surface of the sheath main body on the reference plane or at a position tilted with respect to the reference plane,
the wire is configured to be rotatable with respect to the proximal end region of the sheath main body, and
the wire is configured to have the different bending resistances by including in the region of the wire a plurality of element wires that are arranged so that a region of a high element wire density and a region of a low element wire density are arranged side by side along the reference plane.

2. The treatment instrument of claim 1, wherein the region of the wire is an anisotropic resistance region in which the wire has the different bending resistances in the two directions along the two planes intersecting each other at right angles on the central axis.

3. The treatment instrument of claim 1, wherein the incising portion is configured to protrude from the outer circumferential surface of the sheath main body at a position tilted with respect to the reference plane in a range not greater than 45 degrees from the reference plane.

4. The treatment instrument of claim 1, further comprising:
a braid attached on the distal end region so as to cover an outer circumference of the sheath main body, and
a handle attached to a proximal end of the wire,
wherein
the wire is configured to be rotatable about the central axis in the lumen, and
the wire is attached at a distal end thereof to the braid.

5. The treatment instrument of claim 1, wherein the sheath main body includes a pre-curved portion in the distal end region thereof, the pre-curved portion having a restoring force such that the distal end region of the sheath main body is bent into a bent shape along the reference plane.

6. An endoscope system comprising:
an endoscope including a bendable portion with a channel formed therethrough for receiving a treatment instrument, an elevator configured to raise the treatment instrument while being inserted in the channel, and an observation optical system that is incorporated with the endoscope; and
the treatment instrument configured to protrude from the channel to treat a treatment target, the treatment instrument including:

a sheath main body including: opposed respective distal and proximal end regions along a longitudinal axis, an outer diameter such that the sheath main body is capable of being fit into the channel of the endoscope, and a lumen extending along the longitudinal axis, a wire-shaped incising portion that is configured to engage with the sheath main body so as to protrude from an outer circumferential surface of the sheath main body in the distal end region and extend along the longitudinal axis of the sheath main body, the wire-shaped incising portion being configured to incise a tissue, and a wire that:
is inserted in the lumen of the sheath main body,
includes a region in which the wire has different bending resistances when bent in two directions along two planes intersecting one another at right angles on a central axis of the wire, and
is attached to the distal end region of the sheath main body in a state that one plane of the two planes in the region of the wire is parallel to or coincident with a reference plane of the sheath main body, the reference plane extending along the longitudinal axis of the sheath main body, and the one plane extending along the direction in which the wire has a lower bending resistance, wherein
the incising portion protrudes from the outer circumferential surface of the sheath main body on the reference plane or at a position tilted with respect to the reference plane,
the wire is configured to be rotatable with respect to the proximal end region of the sheath main body,
the sheath main body is configured to be positioned in the channel such that the sheath main body is bent at a distal end portion of the channel by the elevator, the sheath main body being bent in a direction extending along the reference plane, and
the wire is configured to have the different bending resistances by including in the region of the wire a plurality of element wires that are arranged so that a region of a high element wire density and a region of a low element wire density are arranged side by side along the reference plane.

7. A method of using a treatment instrument for incising a tissue, the treatment instrument including:
a sheath main body that includes a lumen and extends along a longitudinal axis thereof,
a wire-shaped incising portion configured to extend from an outer circumferential surface of the sheath main body so as to incise the tissue, and
a wire that:
is inserted in the lumen of the sheath main body,
includes a region in which the wire has different bending resistances when bent in two directions along two planes intersecting each other at right angles on a central axis of the wire, and
is attached to at least a portion of the sheath main body in a state that one plane of the two planes in the region of the wire is parallel to or coincident with a reference plane of the sheath main body, the reference plane extending along the longitudinal axis of the sheath main body, and the one plane extending along the direction in which the wire has a lower bending resistance, the incising portion protruding from the outer circumferential surface of the sheath main body on the reference plane or at a position tilted with respect to the reference plane, and the wire being configured to have the different bending resistances by including in the region of the wire a plurality of element wires that are arranged so that a region of a high element wire density and a region of a low element wire density are arranged side by side along the reference plane, the method comprising:

inserting an endoscope into a body, the endoscope including a bendable portion including a channel for receiving the treatment instrument, the channel being bendable by a bending movement of the bendable portion inside the body, inserting the sheath main body into the channel that is bent in the bendable portion, whereby the sheath main body is rotated together with the wire about the longitudinal axis, inducing the sheath main body to protrude from the channel at a distal end thereof while maintaining the incising portion at a position tilted at an acute angle with respect to the reference plane, inserting into a duodenal papilla the distal end of the sheath main body that is protruded from the channel, and incising the duodenal papilla with the incising portion in a state that the sheath main body is inserted into the duodenal papilla.

8. The method of claim 7, wherein an observation optical system is incorporated with the endoscope so as to permit a user to diagnose inside the body.

* * * * *